United States Patent
Stroem Hansen et al.

(10) Patent No.: US 8,652,095 B2
(45) Date of Patent: Feb. 18, 2014

(54) SKIN RETENTION DEVICE FOR A MEDICAL JET INJECTION KIT

(75) Inventors: Torben Stroem Hansen, Copenhagen (DK); Jens Erik Poulsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/181,126

(22) Filed: Jul. 12, 2011

(65) Prior Publication Data

US 2011/0270217 A1    Nov. 3, 2011

Related U.S. Application Data

(62) Division of application No. 12/158,025, filed as application No. PCT/EP2006/067937 on Oct. 30, 2006, now abandoned.

(60) Provisional application No. 60/757,233, filed on Jan. 9, 2006.

(30) Foreign Application Priority Data

Dec. 20, 2005 (EP) ..................................... 05112490

(51) Int. Cl.
*A61M 5/30* (2006.01)
(52) U.S. Cl.
USPC .......................................................... 604/68
(58) Field of Classification Search
USPC .............................................. 604/68, 69, 70
See application file for complete search history.

(56) References Cited

U.S. PATENT DOCUMENTS

| | | | |
|---|---|---|---|
| 2,398,544 A | | 4/1946 | Lockhard |
| 2,754,818 A | * | 7/1956 | Scherer ........................... 604/68 |
| 5,064,413 A | * | 11/1991 | McKinnon et al. ............. 604/70 |
| 5,836,911 A | | 11/1998 | Marzynski et al. |
| 5,911,703 A | * | 6/1999 | Slate et al. ....................... 604/68 |
| 5,954,689 A | * | 9/1999 | Poulsen .......................... 604/71 |
| 5,957,886 A | | 9/1999 | Weston |
| 6,149,625 A | * | 11/2000 | Weston et al. ................. 604/116 |
| 6,258,059 B1 | | 7/2001 | Weston et al. |

(Continued)

FOREIGN PATENT DOCUMENTS

| | | |
|---|---|---|
| JP | 07255845 | 10/1995 |
| JP | 2000-508928 A | 7/2000 |

(Continued)

*Primary Examiner* — Theodore Stigell
*Assistant Examiner* — Diva K Chander
(74) *Attorney, Agent, or Firm* — Marc A. Began

(57) ABSTRACT

A skin retention device 10 for a medical jet-injection unit 20 having a contact face provided with adhesive 12 in the area surrounding and close to the injection opening(s) 11 of the nozzle 21 which ensures good contact between the nozzle 21 and the skin 30 of a subject in the area chosen for an injection. The injection force can be lowered dramatically. In case of two-stage jet-injections, the initial injection force can be lowered because the skin retention close to the injection point significantly reduces the energy consuming elastic expansion of the skin 30 in the injection area, and the second injection force can be lowered because of the high degree of fixed positioning of the injection opening of the nozzle 21 relative to the injection channel in the skin 30 made during the initial injection stage.

7 Claims, 9 Drawing Sheets

(56) References Cited

U.S. PATENT DOCUMENTS

| | | |
|---|---|---|
| 6,406,456 B1 | 6/2002 | Slate et al. |
| 6,428,528 B2 * | 8/2002 | Sadowski et al. ............. 604/511 |
| 6,537,242 B1 | 3/2003 | Palmer |
| 6,645,169 B1 | 11/2003 | Slate et al. |
| 7,074,210 B2 | 7/2006 | Leon et al. |
| 7,699,802 B2 | 4/2010 | Steinway et al. |
| 2002/0055707 A1 | 5/2002 | Slate et al. |
| 2003/0050592 A1 | 3/2003 | Slate et al. |
| 2006/0089594 A1 | 4/2006 | Landau |
| 2009/0227942 A1 * | 9/2009 | Hansen et al. ................. 604/68 |

FOREIGN PATENT DOCUMENTS

| | | |
|---|---|---|
| WO | WO 98/13087 | 4/1998 |
| WO | WO 00/74763 | 12/2000 |
| WO | WO 01/41863 | 6/2001 |
| WO | WO 01/89613 | 11/2001 |
| WO | WO 01/93931 | 12/2001 |
| WO | WO 02/100276 | 12/2002 |
| WO | WO 03/000320 | 1/2003 |
| WO | WO 03/074102 | 9/2003 |
| WO | WO 2005/058393 | 6/2005 |

* cited by examiner

Fig. 3A
Fig. 3B
Fig. 3C
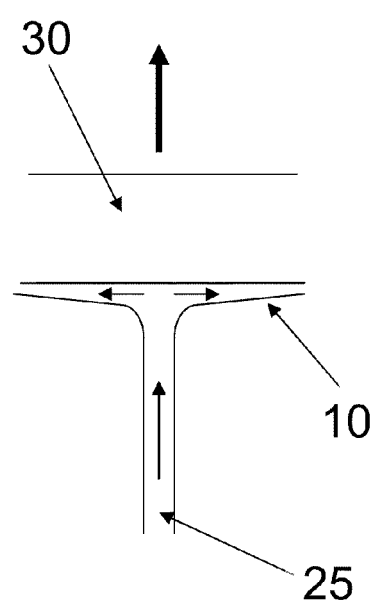
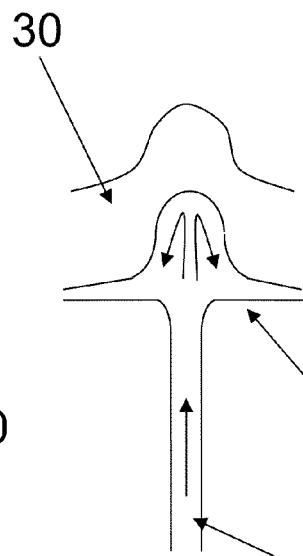
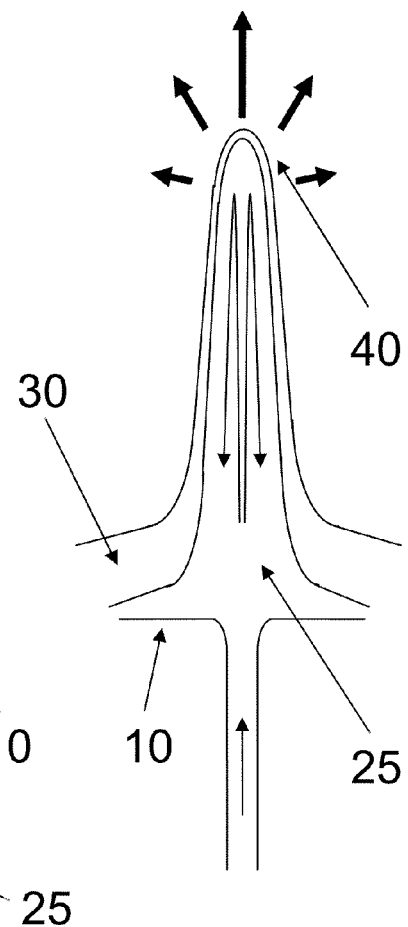

SKIN RETENTION DEVICE FOR A MEDICAL JET INJECTION KIT

CROSS-REFERENCE TO RELATED APPLICATIONS

This application is a Divisional of U.S. application Ser. No. 12/158,025 filed Jun. 18, 2008 which is a 35 U.S.C. §371 national stage application of International Patent Application PCT/EP2006/067937 (published as WO 2007/071485), filed Oct. 30, 2006, which claimed priority of European Patent Application 05112490.7, filed Dec. 20, 2005; this application further claims priority under 35 U.S.C. §119 of U.S. Provisional Application 60/757,233, filed Jan. 9, 2006.

The invention relates to a nozzle device adapted for placement against a skin surface of a subject, the nozzle device providing a tool for retaining and stretching the skin. The nozzle device may advantageously be used in a drug delivery device to improve interaction between the delivery device and a skin surface. For example, the nozzle device may be used in combination with an impulse generating jet injection unit.

BACKGROUND OF THE INVENTION

Subcutaneous and intramuscular delivery of liquid drugs by injection is common in the medical arts. As some medications such as insulin must be given frequently by injection to an individual, easy performance of the injections is desirable.

Many patients dislike needle injections due to pain or fear for needles. Further, blood-borne pathogens, such as HIV and hepatitis, can be transmitted to health care workers by accidental needle-sticks. Also, the disposal of used needles is a growing concern. This disposal presents a problem to individuals other than healthcare workers. Children, for example, may find used needles in the garbage, putting them at risk of contracting infection. Discarded needles likewise pose a risk to waste disposal workers.

In efforts to minimize the fears and risks associated with needle injections, several types of needle-free jet injectors have been developed. These devices penetrate the skin using a high velocity fluid jet and deliver medication into the tissue of a patient. In order to accomplish this, a force is exerted on the liquid medication. Jet injectors in general contain a fluid drug which has been transferred into a chamber having a small orifice at one end. The high velocity fluid jet can be achieved for instance by having a drive means, e.g. a ram, accelerated using either a coil spring or a compressed gas energy source. The ram impacts a plunger which in turn creates a high pressure impulse within the chamber. This pressure impulse ejects the fluid medicament through the orifice at high velocity, piercing the skin. The energy source continues to apply a force to the plunger which quickly propels the drug through the opening in the skin, emptying the syringe in a fraction of a second. The drive means may be adapted to provide a two-stage injection, which is the case for ram mechanisms, i.e. a first penetrating burst of drug at a high pressure followed by a subsequent delivery of the remaining amount of drug at a lower pressure.

During injection the nozzle should be fixed at the same point relative to the skin. If this is not the case, the jet can cause incomplete injections, so called wet shots, where none or only a fraction of the dose is delivered through the skin and the desired blood glucose regulation is jeopardised in case of insulin injection. Another consequence of poor fixation can be lacerations of the skin in case the nozzle moves laterally across the skin during injection.

Addressing this problem, U.S. Pat. Nos. 5,911,703 and 6,406,456 each disclose an injector with an integral suction compartment for pulling the skin against the tip of the injection nozzle. As disclosed, the suction compartment functions to create a seal between the skin area and the injector tip without having to compress the skin area and underlying tissue. Further, the use of a suction compartment can prevent lacerations caused by the injector tip moving relatively to the skin during an injection. WO 03/000320 discloses a jet injection device in which sealing between the nozzle aperture and the skin is secured by a nozzle having a truncated cone configuration to embed in the skin to form a hydraulic seal. In WO 05/058393 a nozzle device with an adhesive to retain the skin against the nozzle device is described, the adhesive is confined to certain areas on the device and the device may have a plurality of skin stretching members or a concave skin stretching member. The device described in U.S. Pat. No. 6,537,242 comprising a cannula also has a concave skin stretching member which can be provided with an adhesive contacting the skin to form a friction enhancing member. In U.S. Pat. No. 6,149,625 an injection aid is disclosed having an adhesive provided around the injection area to maintain the injection aid at the desired location on the skin, the adhesive surrounding the injection area in a diameter of about 5 mm. WO 98/13087 discloses a needle less injector accessory comprising a patch covered on one side with adhesive material to be put on the skin of a subject prior to injection, the injection takes place through the patch material which is pierced by the stream of injectate.

In view of the above, one of the objectives of the present invention is to provide a nozzle device which can be used in combination with a jet expelling device and which aids in providing safe and reliable jet injection of a drug. Also, a main objective of the present invention is to provide a nozzle device which decreases the frequency of incomplete injections while at the same time making it possible to limit the amount of energy required for the jet beam to penetrate the skin. Furthermore, an objective of the present invention is to provide a nozzle device which minimizes the risk of intramuscular injections. The nozzle device should be small in size, easy to use and manufactured cost-effectively.

In the alternative, it is a further objective to provide a jet injection device similar to a conventional pen type injector as regards function and configuration, in order to make the patient comfortable with the jet injection device and so that the jet injection device can easily be utilized by a non-professional user, e.g. a insulin requiring diabetic.

SUMMARY OF THE INVENTION

In the disclosure of the present invention, embodiments and aspects will be described which will address one or more of the above objectives or which will address objectives apparent from the below disclosure as well as from the description of exemplary embodiments.

In a first aspect, a jet injection unit is provided comprising a nozzle portion with an outlet nozzle adapted to be applied to a skin surface of a subject, and a skin retention device comprising a contact face provided with adhesive to be applied in contact with the skin prior to an injection. The adhesive covers a part or all of the contact face, most importantly it surrounds the outlet nozzle opening in a very narrow distance. The adhesive used can have various material characteristics, where some adhesive types may be well suited to adhere on moist surfaces (as sweat covered skin), others can be well suited for hot or cold surfaces. Optionally the contact face can be covered with adhesive with different material characteristics in various segments. In this way, the contact face as a whole will be adapted for a range of situations because each adhesive segment has material characteristics suited for one of the situations. The adhesive segments can be located in different geometrical zones, such as concentric rings, dots and radial zones, the list not being exhaustive. These adhesive segments can have different skin retention force thereby compensating for differences in physical dimensions, climate, skin location etc. The device further comprises impulse generating means for expelling an amount of drug through the outlet nozzle, the impulse generating means being adapted to create a force for injecting liquid drug through the outlet nozzle and into the subject through the skin when the nozzle portion is arranged against the skin of a subject. The device typically comprises a variable-volume impulse chamber associated with the nozzle and on which the impulse generating means acts to empty the chamber. The impulse chamber may e.g. be prefilled, be filled through the nozzle prior to use, or the drug may be transferred to the impulse chamber from a reservoir within the device. Alternatively, a reservoir may serve as an impulse chamber, an impulse applied to the reservoir expelling only a portion of the drug contained in the reservoir.

In order for the jet beam of the jet injection unit to pierce the skin of a subject, a certain strain level is required. When at first the jet beam impacts the skin surface, an elastic expansion takes place before penetration. By narrowing down the inner diameter of the adhesive covered contact face surrounding the jet beam, the elastic expansion can be minimized. This is an expected effect, but studies have shown a remarkable and surprisingly radical increase of the strain index in the thus narrowed injection zone when the inner diameter of the adhesive covered contact face is under a certain limit area. The skin is pierced when a critical strain value is reached which is reflected in the strain index. More particularly, as will be further discussed, when the inner diameter is decreased below approximately 3 mm, the strain index rises significantly more than linearly compared to the decrease and when the inner diameter is decreased below approximately 0.8 mm the strain index rises dramatically, thus creating an earlier crack in the skin for a given penetration speed and pressure. The rise in strain index is so significant that a double advantage over the known art can be achieved: a so far unknown safe and reliable jet injection is ensured, however, by a lower injection force. Hitherto it has been necessary to apply an undesirable high injection force to minimize the risk of wet shots. This has increased the risk of damage caused by intramuscular injections and the risk of altering the pharmaco-kinetics resulting in unpredictable plasma levels of insulin. But when practicing the present invention the risk of wet shots is significantly minimized yet by a lower injection force. The retaining effect achieved by the adhesive not only serves the described purpose of increasing the strain index, but also ensures that the jet beam is positioned above the initially induced opening in the skin throughout the time of the injection, an advantage especially when using a two-stage injection having a lower delivery pressure in the second stage. Further, by providing an adhesive which ensures proper contact between the nozzle and the skin, the compression at the injection site by the user forcing the nozzle too hard against the skin may be omitted, which also reduces the likelihood of injection through the subcutaneous layer and into muscle tissue. Yet another advantage of the invention is that because of the stable and secure fixation of the nozzle orifice relative to the injection opening, the duration of the second, low-pressure injection stage can be prolonged without jeopardizing injection safety. Preferably the second injection stage shall last more than 100 milliseconds, more than 1 second or even up to more than 6 seconds. This allows for the medication to slowly enter the subcutaneous layer and minimize tissue damage.

In a further aspect of the invention, the skin retention device is also adapted to stretch the skin in the proximity of the injection point. The skin stretching means are arranged circumferentially relative to the outlet nozzle, the skin stretching means having an initial first configuration corresponding to an initial state in which the skin stretching means is adapted to be placed against the skin surface of the subject, the skin stretching means being moveable to a second configuration, wherein movement of the skin stretching means to the second configuration after the skin stretching means has been placed against the skin of the subject results in the skin being stretched relatively to the outlet nozzle. By engaging and stretching the skin the likelihood that the nozzle moves relative to the skin during injection is reduced. Further, stretching of the skin will aid in keeping open the injection channel during injection (e.g. through an initially established channel during the first stage of a two-stage injection), the channel subsequently being "closed" as the stretching action is removed.

Depending on the position of the skin-engaging nozzle portion before, during, and after actuation of the skin stretching and stretching means, the skin can be stretched in different ways. For example, when the nozzle portion engages the skin at an early stage, movement of the skin stretching means between the first and second configurations may result in the skin stretching means being displaced proximally relative to the outlet nozzle, thereby stretching the skin "upwardly around" the nozzle portion. If the nozzle portion engages the skin after movement of the skin stretching means between the first and second configurations, the nozzle will engage a radially stretched skin surface. Indeed, a number of combinations are possible, for example the skin may be stretched both radially and upwards relative to the outlet nozzle.

In an exemplary embodiment the skin stretching means is arranged such that the skin is stretched circumferentially away from the outlet nozzle, i.e. similar to a drum skin. The stretching may be accomplished by a flexible skin stretching means which continuously surrounds the outlet nozzle.

When it is defined that the skin stretching means has a second configuration, this does not mean that such a second configuration necessarily is well defined, i.e. the second configuration and the degree of stretching associated therewith may depend on how the nozzle device is used by a user. For example, when the skin stretching means is forced against the skin with a given force the skin stretching means may deflect to a certain degree thereby stretching the skin, whereas the skin stretching means may deflect to a higher degree if the a larger force is applied, this resulting in a greater degree of stretching.

However, the second configuration may also be well defined, for example in case the skin stretching means has a well-defined stop-position or in case the skin stretching means is bi-stable corresponding to the first and second configurations.

Correspondingly, in an exemplary embodiment the skin stretching means comprises a bi-stable member having a generally distally facing surface (i.e. against the skin) circumferentially surrounding the outlet nozzle, the bi-stable member having a distally concave configuration corresponding to the first configuration, and a distally convex configuration corresponding to the second configuration. To engage the skin, adhesive means is arranged corresponding to a peripheral portion of the distal surface, whereby movement of the skin contacting means between the first and second configurations results in the skin contacting means being displaced proximally relative to the outlet nozzle, thereby stretching the skin.

The nozzle and the skin stretching means may be of unitary construction and adapted to be selectively mounted on a jet expelling device, thereby providing a fluid communication between the expelling device and the outlet nozzle. Typically the nozzle portion will comprise a jet outlet nozzle formed therein and terminating at a distal aperture, the outlet nozzle being adapted to create a skin-penetrating jet of a liquid when the aperture is positioned against the skin surface and a liquid is forced through the nozzle at a given pressure. Although reference is made to a single aperture (or nozzle) the nozzle of the invention may comprise any desired number of additional apertures. Further, the nozzle may comprise a pointed hollow needle adapted to penetrate a superficial layer of the skin of a user, thereby aiding the jet of drug to create an opening in the skin from the surface to the subcutaneous space. Such a needle may be relatively short, e.g. 1 mm or less. The nozzle and skin stretching means may be formed integrally with components of a jet expelling system, e.g. a cartridge containing an amount of drug to be injected or in combination with an impulse chamber. The impulse generating means for expelling an amount of drug through the aperture may be configured in any desirable way, for example corresponding to the jet injection devices shown in U.S. Pat. Nos. 5,911,703 and 5,836,911 or US patent applications 2003/0050592 and 2002/0055707.

Alternatively, the nozzle portion and the skin stretching means may be adapted to be releasably coupled to each other. Correspondingly, in a further aspect the invention provides an injection aid adapted to be mounted on an injection nozzle, such an aid corresponding to the above disclosure with the only difference that the nozzle portion has been replaced with means for engaging such a nozzle portion.

The invention further provides a jet expelling device as described above, further comprising a drive assembly for reducing the volume of the impulse chamber with a reduced force relative to the impulse generating assembly when a portion of the drug has been expelled by the impulse generating assembly. The device may comprise a dose titrating unit for selectable setting a dose of drug to be expelled. The selected amount may be transferred to the impulse chamber from a reservoir provided in the device.

In a further embodiment, the invention provides a jet expelling device of the above-described type, further comprising a dose setter for selectable setting a dose of drug to be expelled and transfer that amount of drug from a reservoir to the impulse chamber, an actuator for actuating the impulse generating assembly and the drive assembly, and an actuatable release, wherein actuation of the release causes the impulse generating assembly to expel a portion of the set dose from the impulse chamber at a high pressure through the outlet nozzle, followed by subsequent expelling of the remaining portion of the set dose from the impulse chamber through the outlet nozzle by means of the drive assembly.

The invention also provides a method of introducing an amount of a drug through the skin of a subject, comprising the steps of (a) providing a jet expelling device comprising a nozzle (e.g. of a type as described above), (b) stretching a skin portion of the subject circumferentially relative to a desired skin location for delivery of the amount of a drug, (c) arranging the nozzle against the desired skin location, (d) lifting the skin in the vicinity of the injection point either by force applied by the user or provided by the flex effect of the skin retention device and (e) activating the jet expelling device to generate an impulse for expelling an amount of drug through the nozzle and thereby through the stretched skin portion. Skin stretching means (e.g. of a type as described above) may be associated with the nozzle, whereby the skin portion is stretched when the nozzle is arranged against the desired skin location.

As used herein, the term "drug" is meant to encompass any drug-containing flowable medicine or medicament capable of being passed through a nozzle under high pressure in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin.

DESCRIPTION OF THE DRAWINGS

In the following the invention will be further described with references to the drawings, wherein

FIG. 3 shows three sequences of the initial phase of an injection in the injection zone.

In the figures like structures are generally identified by like reference numerals.

DESCRIPTION OF EXEMPLARY EMBODIMENTS

When in the following terms as "distal", "proximal" and "radial" or similar relative expressions are used, these only refer to the appended figures and not necessarily to an actual situation of use. The shown figures are schematic representations for which reason the configuration of the different structures as well as there relative dimensions are intended to serve illustrative purposes only.

Figure 1:
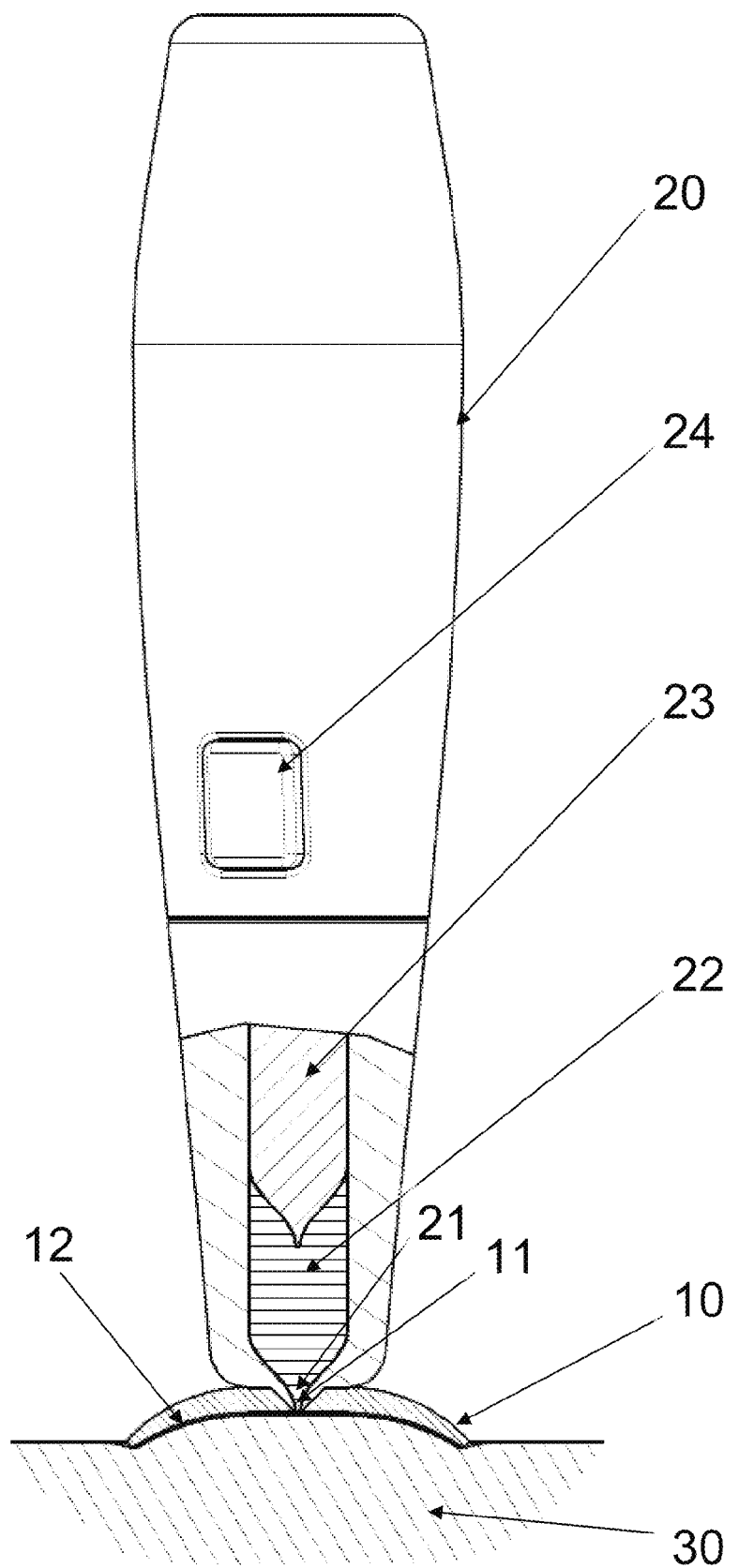
FIG. 1 shows a side view of a jet injection unit and a skin retention device, the lower part of the unit and the skin retention device in sectional view.

FIG. 1 shows a side view of a jet injection unit 20 and a skin retention device 10 connected thereto. The lower part of the unit is shown in sectional view to show the piston 23 slidingly arranged in a housing thereby defining a variable-volume impulse chamber 22 in flow communication with the aperture through a nozzle conduit 21. In the shown embodiment the impulse chamber is adapted for being filled with a liquid drug by suction through the nozzle conduit by moving the piston 23 proximally, however the impulse chamber unit 22 may also be provided with an opening in either the housing or the piston 23 allowing a drug to be introduced therethrough by either suction or external pressure in which case the nozzle aperture 21 should be closable. The skin retention device 10 connects the injection unit 20 to the skin 30 of a subject by means of the adhesive 12 provided on the contact face. The adhesive surrounds the injection opening 11 of the retention device 10, said opening 11 is in close communication with the nozzle 21 for injecting the liquid drug when the injection button 24 is activated.

Figure 2:
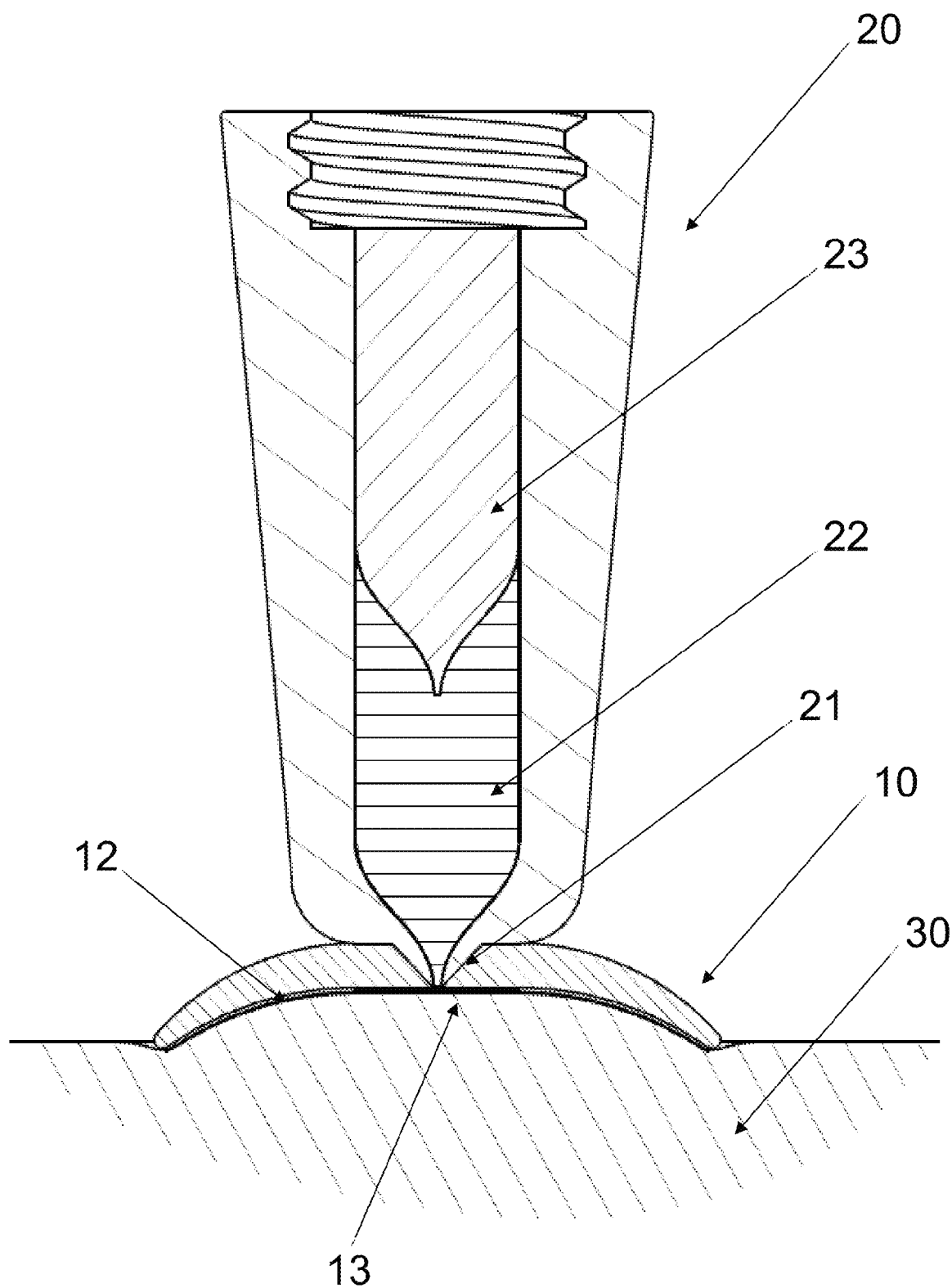
FIG. 2 shows a sectional view of a skin retention device and the lower part of a jet injection unit.
Figure 7:
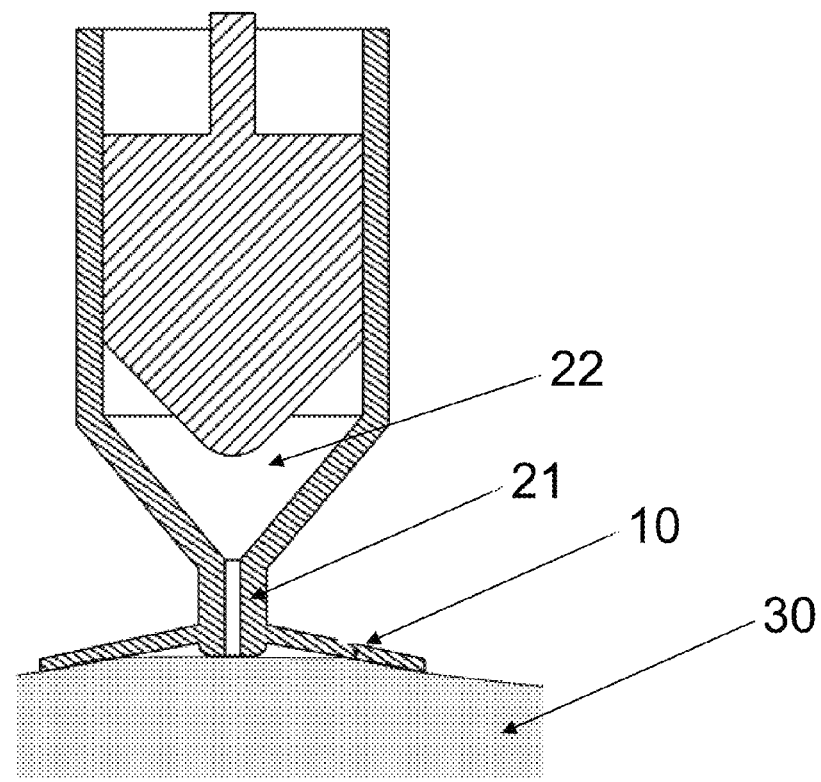
FIG. 7 shows a sectional view of the lower part of a jet injection unit and a skin retention device in a first configuration.
Figure 8:
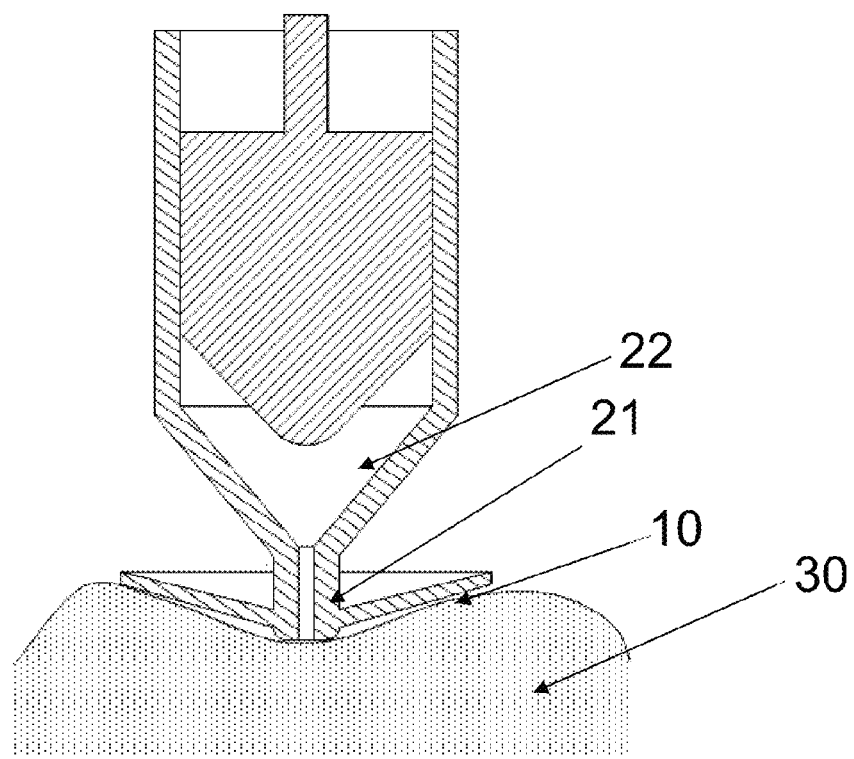
FIG. 8 shows a sectional view of the lower part of a jet injection unit and a skin retention device in a second configuration.
Figure 9:
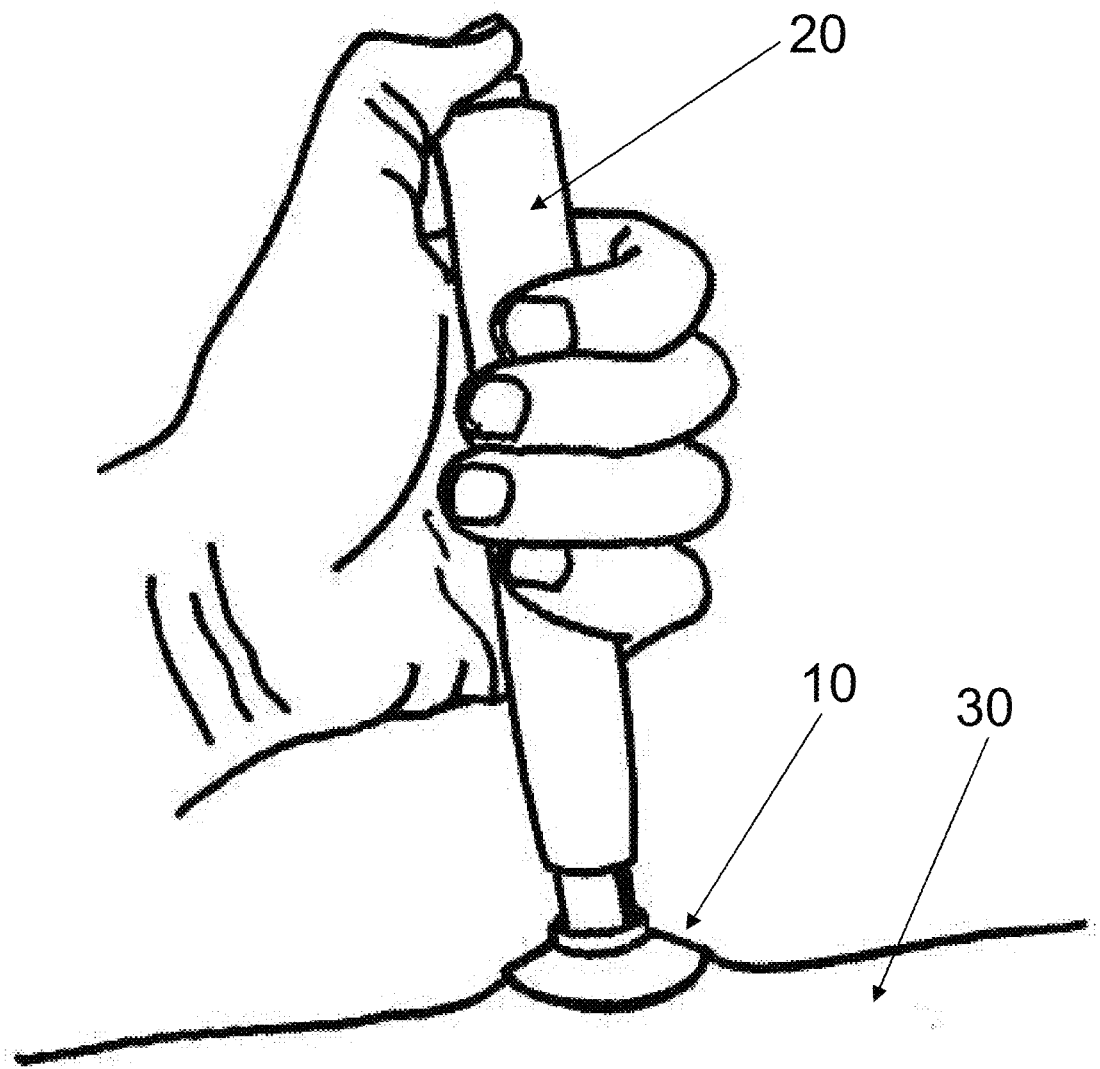
FIG. 9 shows a jet injection with a skin retention device in use during injection.
Figure 10:
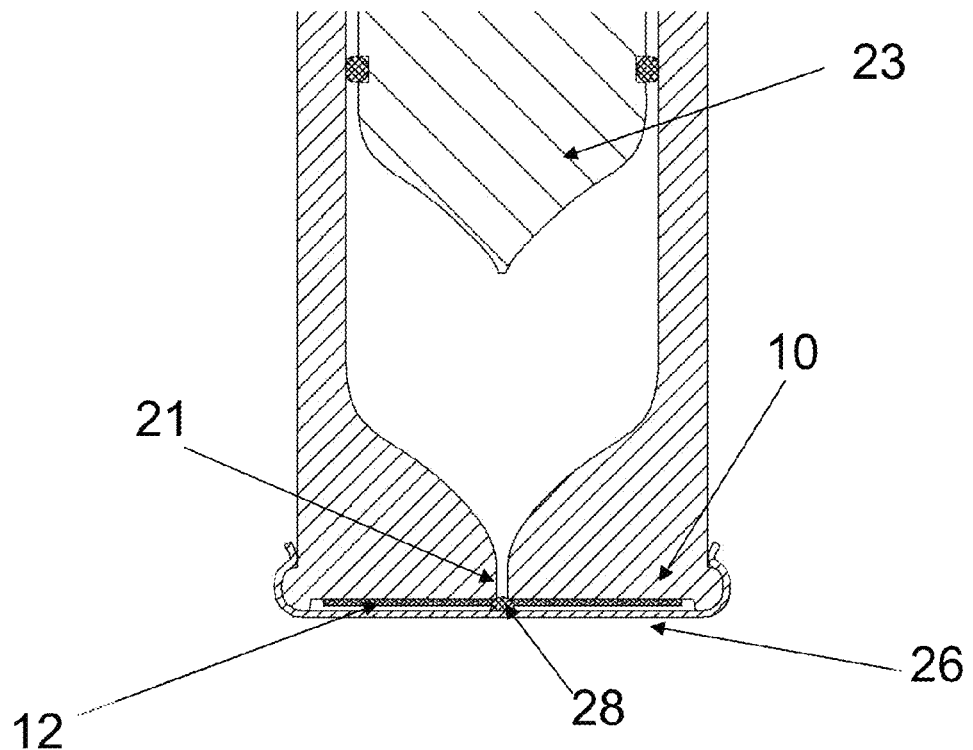
FIG. 10-13 shows a jet injection device integrated with the skin retention device comprising various protective covers and a plug.
Figure 11:
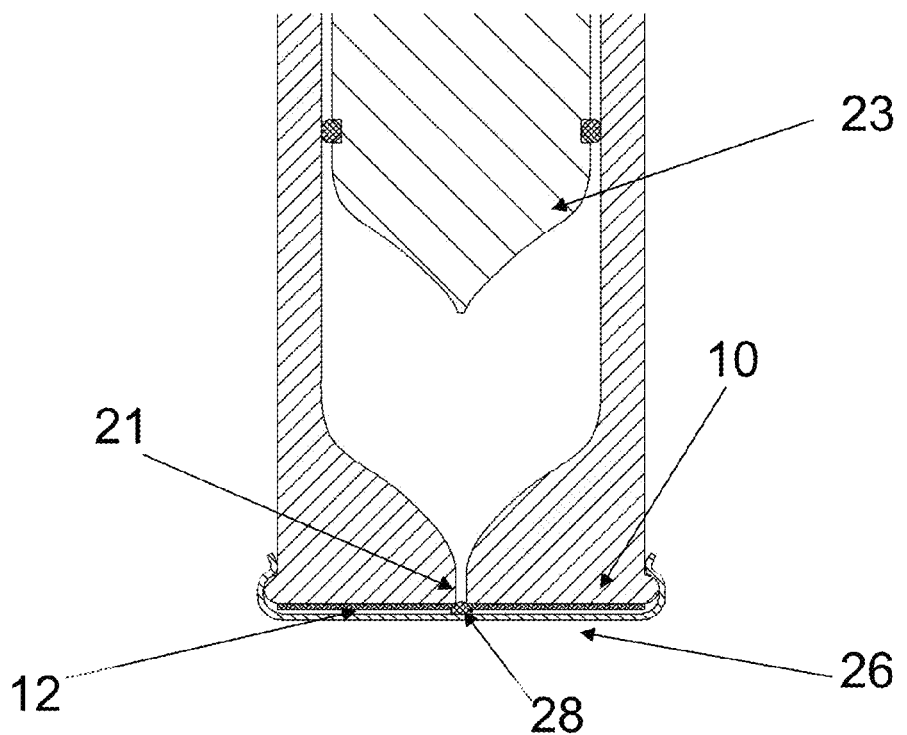
Figure 12:
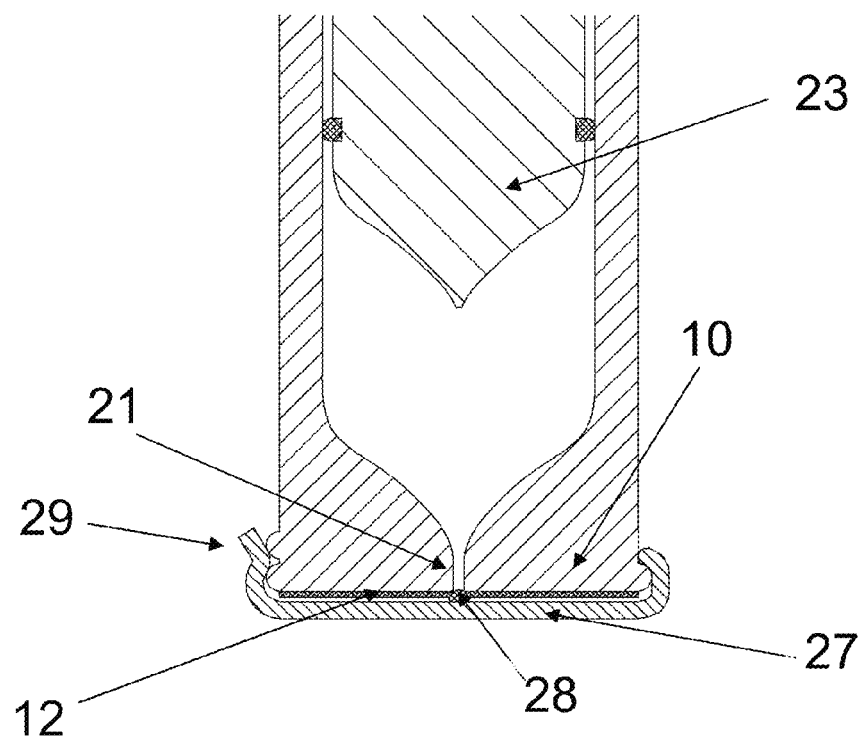

FIG. 2 shows in greater detail the skin retention device 10 when contacting and retaining the skin 30 just prior to an injection. When supplied, the skin retention device 10 will preferably have a protective peel-able film (not shown) covering the adhesive 12. When preparing for an injection, the user will peel off the protective film and by holding the injection unit 20 press the retention device 10 against the skin 30 on the location where the injection is desired. Further the retention device can comprise a plug sealing off the injection opening (not shown) to ensure integrity of the contained liquid and minimize evaporation. The plug can be fixed in various ways: It can be fixed to the inside of a hard cover protecting the contact face, it can be pressed against the injection opening by a flexible cover, and it can be in various shapes either covering the injection opening or sealing it by partly entering and press on the inside walls of the injection opening—this list not being exhaustive. The contact face of the retention device can have various shapes, flat or curved. The flat surface has production advantages, whereas the curved shapes can have positive performing effects. In the embodiment on FIG. 2, the retention device 10 has a distal convex shape. The user shall apply sufficient force on the retention device 10 to ensure good contact between the retention device 10, via the adhesive 12, to the skin 30 on all off the contact face covered by adhesive 12. When doing this, a stretch of the skin 30 is applied radial away from the injection point, this process can be seen on FIGS. 7 and 8. Once this is done, the user can ease off the pressing force or even apply a drawing force through the injection unit 20 to the retention device 10 as shown on FIG. 9, which will have the effect that the skin 30 in the injection area is drawn away from the underlying tissue, thereby minimising the risk of injection into muscle tissue. This is achieved by means of the adhesive layer 12, which also ensures that the stretch of the skin 30 and the correct position of the nozzle 11 over the injection point is maintained throughout the injection period. FIGS. 7 and 8 further illustrates a specific embodiment, comprising a bi-stable retention device 10. Thus the retention device 10 has an initial configuration (FIG. 7) in which it is adapted to be placed against the skin 30 surface of the subject, and being movable to a second configuration (FIG. 8) where the retention device 10 in a "flip-flop" manner presses the injection opening of the nozzle 21 against the skin 30 while stretching the skin 30 in the area in contact with the contact face, by lifting the skin 30 surrounding the injection point.

Figure 13:
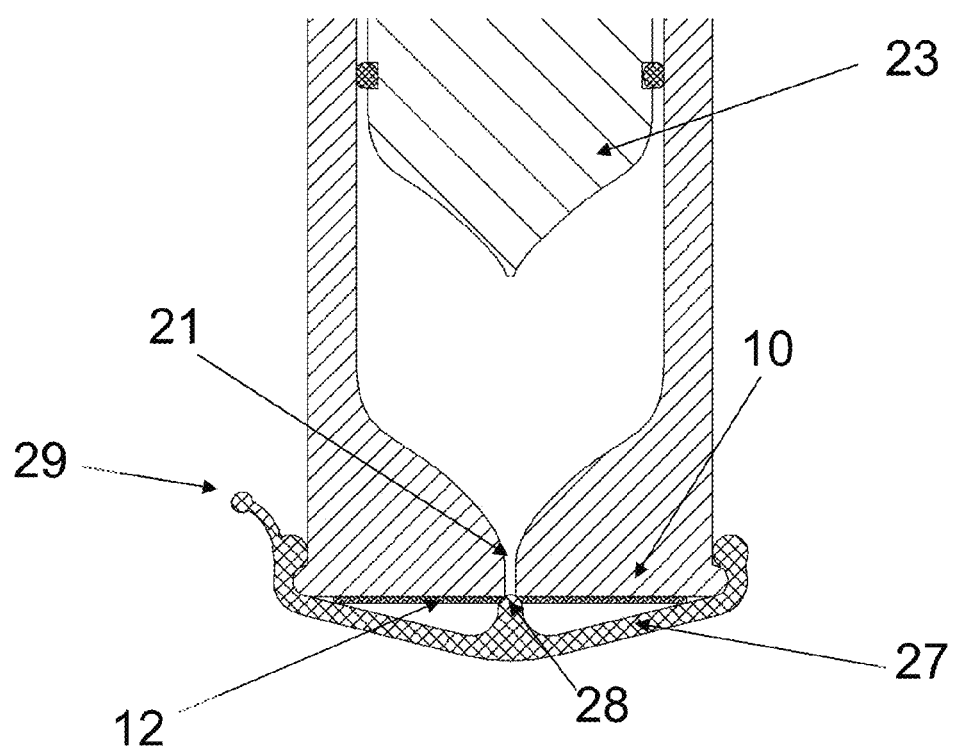

A close interaction between the nozzle 21 and the retention device 10 in the injection zone is achieved by the chamfered outline of the nozzle 21 in the contact zone, which can be seen close up on FIG. 2. This has the important advantage that the adhesive 12 can ensure retention of the skin 30 very close to the injection point, enabling the inner diameter 13 of retention to be very small. In another embodiment of the invention (not shown), the same result can be reached by making the face of the nozzle 21 which contacts the skin 30, flush with the contact face of the retention device 10; adhesive 12 can then be applied on both surfaces, thereby making the nozzle 21 face an integrated part of the retention device 10 contact face, whereby the inner diameter 13 of the adhesive covered contact face is no bigger than the actual diameter of the nozzle 21 orifice. Even if the face of the nozzle 21 is not flush with the retention device 10 contact face, this effect can still be achieved, as long as the nozzle 21 face is covered with adhesive 12 to a narrow diameter. In yet another embodiment shown on FIG. 10-13 making the nozzle 21 face an integrated part of the retention device 10 contact face is achieved by manufacturing the nozzle 21 and the retention device 10 in one piece for example in a moulded polymer or a blend of a polymer and an elastomer material. This gives advantageous low production costs, and a simple device. The drawback is, that the skin retention device 10 can not be flexible and/or bi-stable as seen on FIG. 7 and FIG. 8. but when sufficient initial applying force is preformed by the user, skin 30 stretching, adhering and skin 30 lifting once the applying force is eased off, can still be achieved even with a not-flexible, convex contact surface. On FIGS. 10 and 11 a concept is shown where a stiff protecting cover 26 is attached to the integrated retention device and nozzle, done by any known technique such as a thread, bayonet coupling or a clamping as shown. A plug 28 either entering the orifice or just pressing on the edge of the orifice ensures closure and integrity of the nozzle thereby minimizing evaporation of the liquid, In FIG. 10, a ridge on the rim of the contact face ensures distance between the adhesive layer and the inner surface of the cover, in FIG. 11 this is ensured only by the stiffness of the cover material and the distance to the adhesive layer provided by the plug 28. Further, it can also be possible to let the cover have contact to the adhesive layer depending on the material characteristics. The cover can be made of moulded material analogue to the material of the nozzle itself, by a metal such as aluminium or any known adequate material. In a slightly different concept shown on FIGS. 12 and 13, the cover material 27 is flexible whereby the connection to the nozzle can be ensured by stretching the rim of the flexible cover over the rim of the nozzle/contact face, analogue to FIGS. 12 and 13, a plug 28 is provided to ensure integrity of the content of the nozzle. In FIG. 13 the flexibility of the cover material is utilized not only to fix the cover to the device, but also to apply a down force on the plug towards the orifice. Further in FIGS. 12 and 13 an "ear" 29 is provided to ensure a save grip when the cover is taken off. The concepts shown on FIG. 10-13 are not exhaustive, further variations can be used such as peel off covers adhered to the device, with or without a plug, or devices with a cover but without adhesive material, where the adhesive can be a double sided gluing film applied to the skin and the contact surface of the device immediate prior to injection, where the injection jet beam penetrates both the gluing film and the skin.

Figure 4:
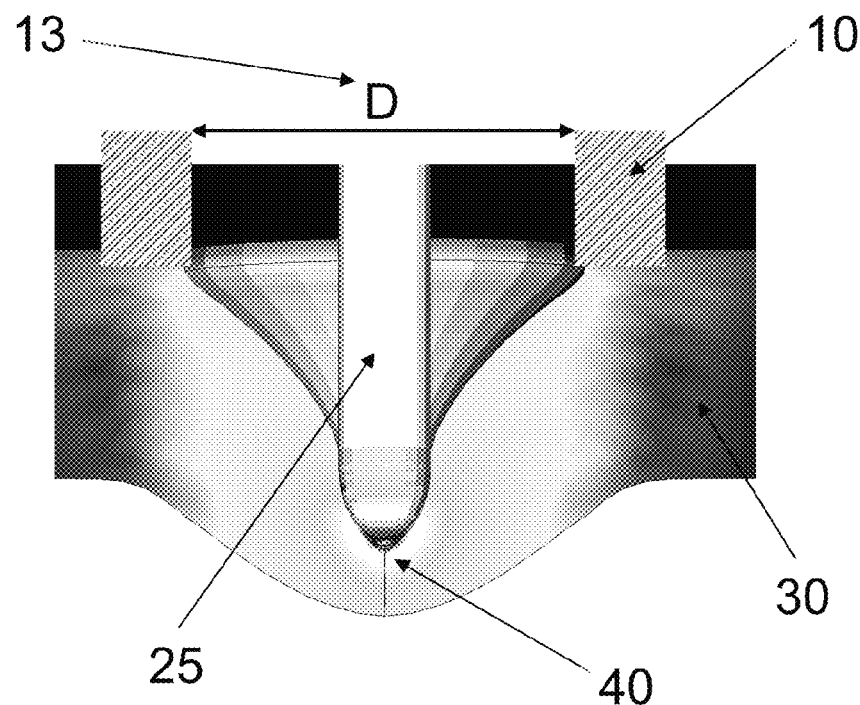
FIG. 4 shows a close up perspective view of the injection zone in an initial phase of an injection.
Figure 5:
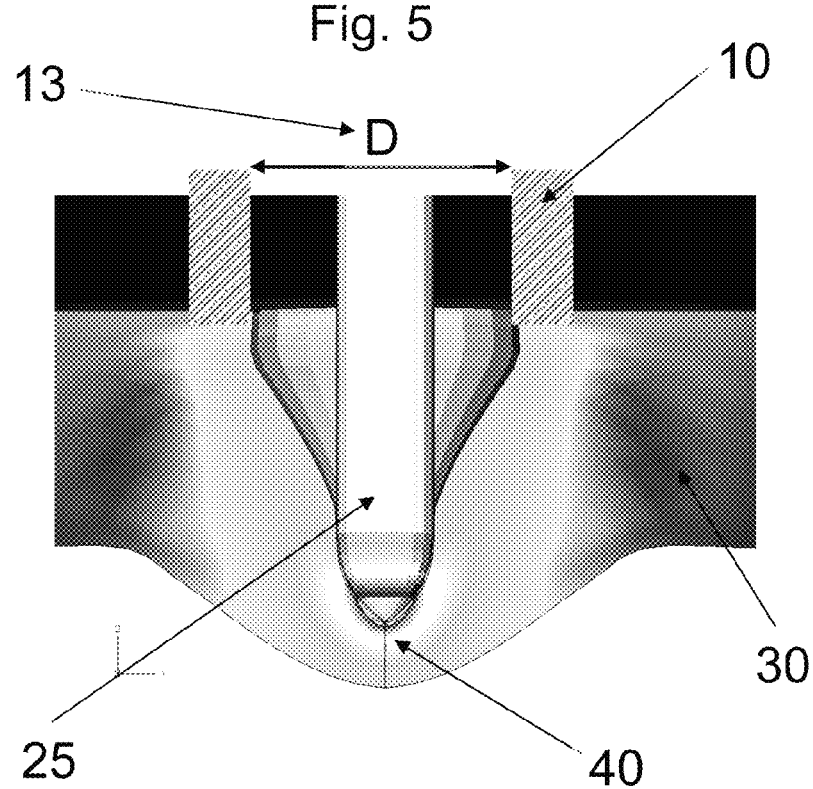
FIG. 5 shows a close up perspective view of the injection zone in an initial phase of an injection with smaller inner diameter of retention.

FIGS. 3, 4 and 5 shows the course of a jet injection in the injection zone. FIG. 3 shows the beginning of an injection where the jet beam 25 reaches the skin 30 surface, fills out the present void between the skin 30, the nozzle 21 face and the retention device 10 and builds up pressure which leads to an elastic expansion of the skin 30 before penetration. In FIG. 3C the maximum strain index is illustrated at position 40. The effect that the inner retention diameter 13 (the inner diameter of the adhesive covered area of the retention device 10) has on the skin stretch (strain) level due to jet beam 25 impact can be seen on FIG. 4 and FIG. 5. These figures shows two different retention cases where the jet beam 25 penetration speed and pressure are the same in both cases, but where the inner retention diameter 13 is 1 mm in FIG. 4 and 0.6 mm in FIG. 5. As can be seen, in the case of the smaller retention diameter 13, the strain level 40 is significantly bigger, which means that penetration of the skin 30 is reached at an earlier stage. As the inner retention diameter 13 is decreased, so is the energy absorbing elastic expansion of the skin 30 before penetration. And as the energy absorption before penetration is decreased, the energy (pressure) applied to the jet beam 25 can be decreased accordingly, while keeping the same or better security of penetration. Pressure applied and risk of tissue damage is decreased while injection safety is increased.

Figure 6:
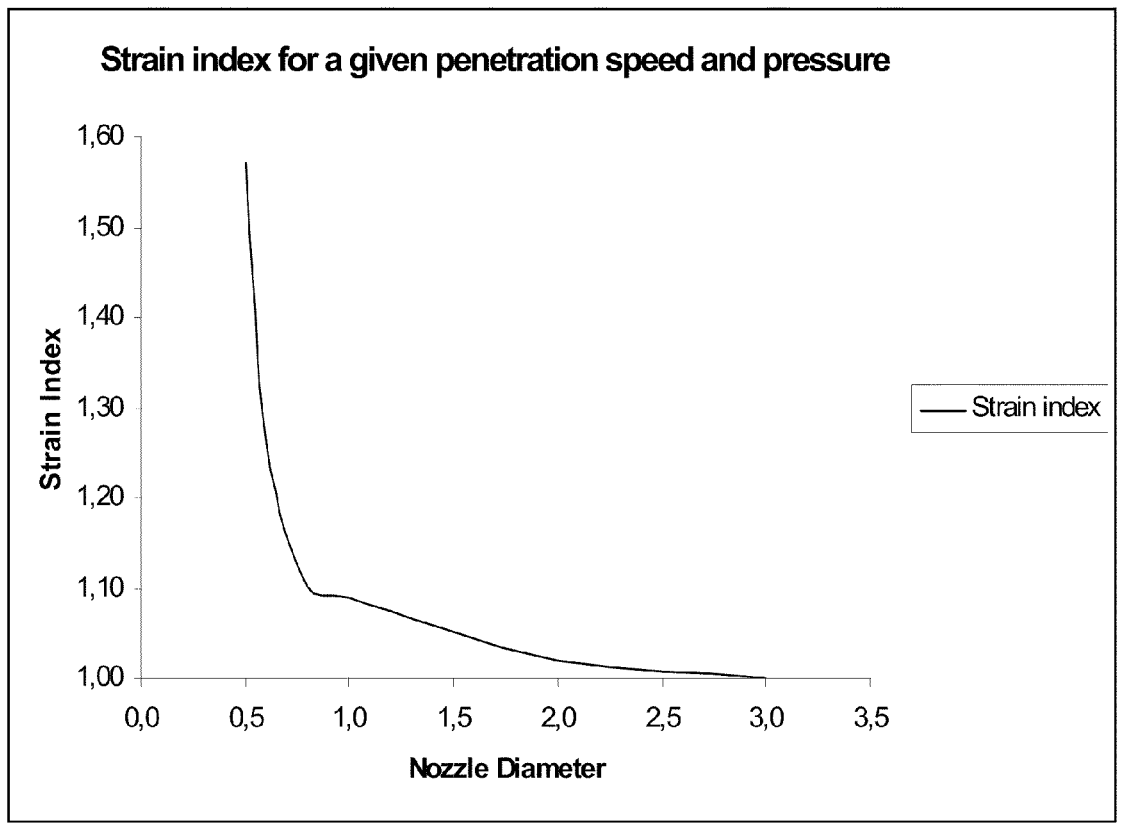
FIG. 6 a graph showing the coherence between train index and inner diameter of retention.

While this relative connection between inner retention diameter 13 and strain index 40 might be expected, studies have shown a surprising development when reaching a certain diameter 13 level. FIG. 6 shows how the strain index is slowly rising with falling retention diameter 13 until a certain small diameter 13 level is reached, where the strain index rises dramatically with falling retention diameter 13. For the given penetration speed and pressure shown on FIG. 6 the strain index rises dramatically when the retention diameter 13 falls under approx. 0.8 mm, however the area where this development is achieved can vary with different jet beam 25 penetration speeds and pressures.

The invention claimed is:

1. Skin retention device (10) for a medical jet-injection unit (20) comprising a contact face provided with adhesive (12) to be applied in contact with the skin (30) of a subject prior to an injection, said contact face further being provided with at least one injection opening (11), wherein the adhesive (12) substantially surrounds the injection opening(s) (11) in the proximity of the opening(s), such that skin retention against the contact face close to the injection opening(s) (11) is ensured, the energy required for the jet beam (25) to penetrate the skin (30) is limited and exact fixation of a jet beam (25) over the injection point throughout the injection period is ensured, wherein the adhesive (12) substantially surrounds the injection opening(s) (11) in a diameter (13) smaller than 3 mm.

2. The skin retention device (10) according to claim 1, wherein the adhesive (12) substantially surrounds the injection opening(s) (11) in a diameter (13) smaller than 0.8 mm.

3. The skin retention device (10) according to claim 1, wherein the adhesive (12) substantially surrounds the injection opening(s) (11) in a diameter (13) smaller than 0.6 mm.

4. The skin retention device (10) according to claim 1 wherein the contact face has a convex shape.

5. The skin retention device (10) according to claim 1 wherein the retention device (10) comprising a contact face is an integrated part of the jet-injection unit (20).

6. The skin retention device (10) according to claim 1, wherein the jet-injection nozzle (21) and the contact face is manufactured in one piece, whereby the contact face is a part of the nozzle (21).

7. The skin retention device (10) according to claim 1, wherein the contact face has a cone shaped geometry providing an even stretch of the skin (30) radial outwards from the injection opening(s) (11) and providing lift of the skin (30) away from the subject without any force performed by the subject, once the skin retention device (10) has been applied in contact with the skin (30).

* * * * *